United States Patent [19]

Wood et al.

[11] Patent Number: 4,482,387

[45] Date of Patent: Nov. 13, 1984

[54] POWDERED WAX, TABLET COATED THEREWITH AND METHOD

[75] Inventors: Thomas G. Wood, East Brunswick; Steven M. Oblack, South Plainfield, both of N.J.

[73] Assignee: E. R. Squibb & Sons, Inc., Princeton, N.J.

[21] Appl. No.: 557,705

[22] Filed: Dec. 2, 1983

Related U.S. Application Data

[62] Division of Ser. No. 397,635, Jul. 12, 1982, Pat. No. 4,456,629.

[51] Int. Cl.³ ............................................. C08L 91/06
[52] U.S. Cl. .................................... 106/270; 208/24; 208/21
[58] Field of Search .................... 106/270; 208/24, 21; 427/3

[56] References Cited

U.S. PATENT DOCUMENTS

| | | | |
|---|---|---|---|
| 2,982,234 | 5/1961 | Ackley | 424/6 |
| 3,116,205 | 12/1963 | Heilig | 424/6 |
| 3,438,797 | 4/1969 | Biddle | 424/6 |
| 3,533,804 | 10/1970 | Bennett | 424/6 |
| 3,576,665 | 3/1971 | Cheiken | 427/3 |

FOREIGN PATENT DOCUMENTS 842613  7/1960  United Kingdom ................... 424/6

*Primary Examiner*—Sam Silverberg
*Attorney, Agent, or Firm*—Lawrence S. Levinson; Burton Rodney

[57] ABSTRACT

A novel powdered wax is provided which is especially adapted for use as a polishing agent for tablets and as a substrate for print carried by such tablets. A method for forming such powdered wax is also provided which includes the steps of milling pieces of wax with dry ice and then allowing the dry ice to evaporate while maintaining the milled wax at cool temperatures to prevent clumping.

7 Claims, No Drawings

POWDERED WAX, TABLET COATED THEREWITH AND METHOD

This is a division of application Ser. No. 397,635, filed Jul. 12, 1982 now U.S. Pat. No. 4,456,629.

FIELD OF THE INVENTION

The present invention relates to a powdered wax particularly suited for use as a tablet polishing wax which (wax) is to carry print, to tablets polished with such wax, and to a method for preparing such powdered wax.

BACKGROUND OF THE INVENTION

It is standard practice in the pharmaceutical industry to coat or polish printed sugar tablets with waxes applied in a chlorinated or flammable hydrocarbon solvent to achieve a shiny gloss and protection for the print. Thus, typically, a print base solution containing ethanol, water, ethyl cellulose and shellac is applied to the tablets, the tablets are dried and then the dried tablets are printed. During the printing operation, talc is applied to enable the tablets to feed properly in the printing machine. After printing, the tablets are loaded into a polishing pan and a wax solution formed of various conventional waxes in a chlorinated or hydrocarbon solvent is applied over the print.

Although the above procedure has achieved some commercial success, it has been found to be lacking in several respects. The use of chlorinated solvents in the wax emulsion has been found to create a potential health problem while the use of talc in connection with the printing machines has been found to create a sanitary problem. Moreover, it unfortunately has been found that the wax coating is quite soft and does not readily protect the print. Further, if the wax coating is first applied and the tablet printed over the wax coating, the print is easily rubbed off.

It is also known to polish tablets with powdered carnauba wax. However, the shine is too hard to serve as a substrate for printing.

Accordingly, it is seen that a need exists in the tablet polishing and printing art for a wax coating and polish for tablets which will not only provide a durable shiny coating but also a substrate for printing which will retain print for extended periods.

DESCRIPTION OF THE INVENTION

In accordance with the present invention, a wax is provided which is in a fine powdered state having an average particle size of less than about 100 microns and preferably less than about 90 microns. The powdered wax of the invention is preferably comprised of beeswax (also referred to as white wax), or mixtures of beeswax and carnauba wax, although one or more other waxes may be employed in combination with the beeswax and/or carnauba wax or by themselves. Examples of such other waxes suitable for use herein include, but are not limited to, paraffin wax, polyethylene glycol waxes, other hard waxes such as candelilla wax, ozokerite, oricury, microcrystalline wax and the like.

The powdered wax of the invention may be applied as a polish to tablets to produce a durable shiny protective coating. Furthermore, the wax coating may be printed over with the print being retained for extended periods of time. In fact, the overall appearance and durability of both the print and shine is superior to that of conventionally wax-coated and printed tablets.

In addition, in accordance with the present invention, a method is provided for preparing the powdered wax described above, which method includes the steps of providing a desired wax formulation, melting the wax formulation to form a homogeneous mass, allowing the wax formulation to harden, breaking the hardened wax formulation into small pieces, milling the small pieces of wax with dry ice employing a weight ratio of wax to dry ice of within the range of from about 0.5:1 to about 5:1, preferably from about 0.5:1 to about 2:1, and then allowing the dry ice to evaporate from the milled wax formulation while maintaining the wax at a temperature of below about 5° C., thereby leaving the wax in a fine powdered state free of clumps.

In carrying out the above method, the homogeneous melted wax formulation is preferably frozen before it is broken up into small chunks prior to milling. The size of the small chunks of wax to be milled is not critical. However, for convenience, it is preferred that the wax be broken up into pieces of from about 1 to 5 microns up to about 1 to 10 centimeters in size to facilitate milling.

The milling of the frozen pieces of wax with dry ice is carried out employing conventional high speed milling apparatus such as a Fitzpatrick mill employing hammers forward through a small herring bone screen. However, other conventional milling equipment may be employed as will be apparent to those skilled in the art.

The milling procedure may be carried out as a one step procedure. However, it is preferred that the milling step be carried out stepwise so that a first portion of the dry ice will first be milled, thereafter a second larger portion of dry ice together with milled dry ice will be mixed with the wax chunks and the mix milled, and finally the remainder of the dry ice will be milled with the wax-dry ice mixture.

After the wax is milled with dry ice, a snow of dry ice and wax is formed which is kept in a cooled state as the dry ice is allowed to evaporate. The snow may be placed in conventional refrigeration apparatus to maintain the snow at a temperature of within the range of from about −5° to about 5° C. If during the dry ice evaporation period, the wax is allowed to reach temperatures of greater than about 10° C., the wax will form clumps as opposed to the desired fine powder.

The powdered wax produced by the method of the present invention is particularly suited as a polishing agent and print substrate for tablets. In fact, heretofore, where it has been attempted to powder wax, the result has been melted globs or a semi-powder-like wax product replete with clumps and therefore unsatisfactory as a polishing agent for tablets.

The following Examples represent preferred embodiments of the present invention. All temperatures are expressed in °C.

EXAMPLE 1

A fine powdered wax containing equal parts of carnauba wax and white wax particularly suitable for use as a polishing agent for sugar-coated tablets was prepared as described below.

Carnauba wax (10 kg) and white wax (10 kg) were placed in a suitably sized container and melted at 100°. The melted homogeneous wax mix was then placed in a freezer maintained at −10° C. for four hours. The resulting frozen block of wax was removed from the freezer, placed in a cloth and then broken into small chunks of average size of less than 2 inches. The wax chunks were immediately milled with dry ice in a Fitzpatrick impact mill with hammers forward high speed through a 0.15" by 17/32" long herring-bone or finer herring-bone screen, as follows. 1 Kg of milled dry ice was milled with 13 kg of dry ice chunks together with all 20 kg of the wax mix. Thereafter, the milled dry ice-wax mix was milled with another 1 kg portion of dry ice. A dry ice/wax snow was thereby formed which was spread on a tray. The tray was placed in a refrigerator maintained at about 4° C., for 12 hours, thereby allowing the dry ice to evaporate and leaving fluffy powdered wax having a fineness of 100% through #60 mesh screen and over 25% through #400 mesh screen on an Alpine sieve.

The so-formed powdered wax was placed in an airtight container and refrigerated until used.

The 50—50 carnauba wax-white wax powder was applied as a polishing agent for sugar coated tablets to produce a durable quality shiny coating without the need for use of chlorinated hydrocarbon solvents or flammable hydrocarbon solvents. The so-polished tablets were printed over to form a durable print which was not easily rubbed off.

EXAMPLE 2

A fine powdered pure white (beeswax) wax was formed employing the procedure as described in Example 1 except that all carnauba wax was replaced with white wax.

The resulting powdered white wax was found to be of the same fineness as the Example 1 wax.

What is claimed is:

1. A method for forming a powdered wax formulation which comprises milling frozen pieces of wax and dry ice to form a snow-like mixture, allowing the dry ice to evaporate from the mixture at a temperature of less than about 5° C. a dry powdered wax which is substantially free of clumps and having an average particle size of less than 100 microns, said wax comprises a wax selected of white wax, caranula wax and mixtures thereof.

2. The method as defined in claim 1 wherein the wax comprises a wax selected from the group white wax and polyethylene glycol wax, caranula wax and polyethylene glycol wax, and mixtures thereof.

3. The wax formulation as defined in claim 1 wherein the wax is a mixture of white wax and carnauba wax.

4. The wax formulation as defined in claim 1 wherein the wax is an equal parts mixture of white wax and carnauba wax.

5. The wax formulation as defined in claim 1 wherein the dry ice will be employed in a weight ratio to the wax of within the range of from about 0.5:1 to about 5:1.

6. The method as defined in claim 1 including the steps of first melting the wax to form a melted homogeneous mixture.

7. The wax formulation as defined in claim 1 wherein the wax is comprised of a mixture of carnauba wax and white wax, or a mixture of carnauba wax and/or white wax with one or more of paraffin wax, polyethylene glycol waxes, candelilla wax, ozokerite, oricury of microcrystalline wax.

* * * * *